United States Patent [19]

Snyder et al.

[11] Patent Number: 4,595,681

[45] Date of Patent: Jun. 17, 1986

[54] ANTIHYPERTENSIVE NEUTRAL LIPID

[75] Inventors: Fred L. Snyder; Merle L. Blank, both of Oak Ridge, Tenn.

[73] Assignee: The United States of America as represented by the United States Department of Energy, Washington, D.C.

[21] Appl. No.: 665,214

[22] Filed: Oct. 26, 1984

[51] Int. Cl.$^4$ ............... A61K 31/22; A61K 33/42
[52] U.S. Cl. .................... 514/77; 260/403; 514/546; 560/263
[58] Field of Search ............... 560/263; 514/546, 77; 260/925

[56] References Cited
U.S. PATENT DOCUMENTS 4,329,302  5/1982  Hanahan et al. .................. 260/925

OTHER PUBLICATIONS

Renooij et al., Biochimica et Biophysica Acta, vol. 663, (1981), pp. 545–556.

*Primary Examiner*—Richard L. Raymond
*Attorney, Agent, or Firm*—Irving Barrack; Stephen D. Hamel; Judson R. Hightower

[57] ABSTRACT

The invention relates to the discovery of a class of neutral acetylated ether-linked glycerolipids having the capacity to lower blood pressure in warm-blooded animals. This physiological effect is structure sensitive requiring a long chain alkyl group at the sn-1 position and a short carbon chain acyl group (acetyl or propionyl) at the sn-2 position, and a hydroxyl group at the sn-3 position.

3 Claims, 1 Drawing Figure

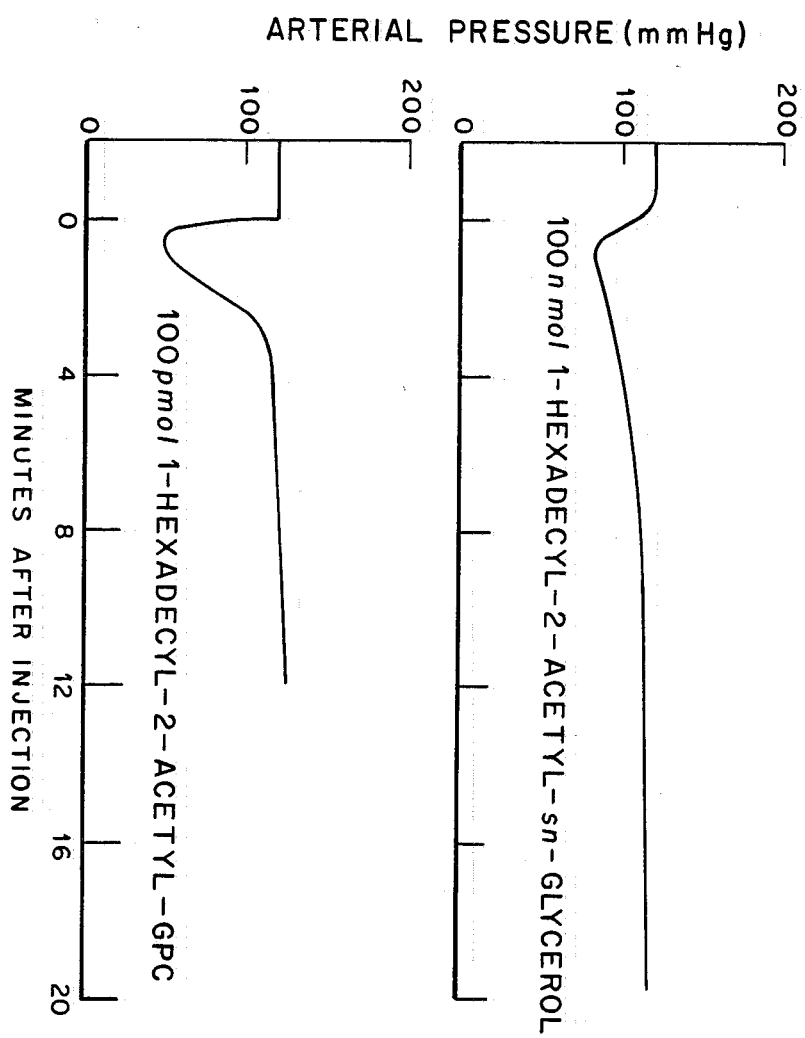

ANTIHYPERTENSIVE NEUTRAL LIPID

This invention is a result of work under Contract No. DE-AC05-76OR00033 between Oak Ridge Associated Universities and the U.S. Department of Energy.

BACKGROUND OF THE INVENTION

The present invention relates generally to the discovery of a unique class of antihypertensive neutral lipids and it is an object of the invention to teach the use of a class of neutral glycerolipids to lower the arterial blood pressure of warm-blooded experimental animals. The term antihypertensive neutral lipid refers to a 1-alkyl-2-short chain carbon acyl-sn-glycerol.

In our co-pending U.S. patent application Ser. No. 232,790 filed Feb. 9, 1981, we describe and claim a class of alkyl acetylated phosphocholine compounds which can be synthesized from choline-containing plasmalogens extracted from beef heart containing 16–18 carbon alkyl moieties. By appropriate reduction and acetylation therein described, 1-alkyl-2-acetyl-sn-glycero-3-phosphocholine compounds also known as platelet activating factor and hereinafter referred to as PAF are produced which, when administered either intravenously or orally to hypertensive (or normal) animals, result in a profound lowering of arterial pressure.

SUMMARY OF THE INVENTION

We have discovered that a class of neutral acetylated ether-linked glycerolipids, having a different structure than PAF and which are chemical and metabolic precursors to PAF-type compounds, have a similar but distinguishable effect on blood pressure of warm-blooded animals.

The blood-pressure lowering capacity of the selected neutral glycerolipids is structure sensitive requiring the existence of a 12–20 carbon alkyl group at the sn-1 position, a short-carbon chain acyl group at the sn-2 position and a hydroxyl group at the sn-3 position. In addition to the specific structure sensitivity as a function of physiological response, the neutral lipids of this invention are themselves precursors of and convertible to antihypertensive-inducing PAF-type 1-alkyl-2-acetyl-sn-glycero-3-phosphocholine by enzymatic conversion via choline phosphotransferase, a cytidine diphosphocholine-dependent enzyme, as described in a Biochimica Biophysica Acta, pp. 545–556, Vol. 663 (1981). This enzyme transfers the phosphocholine moiety to the sn-3 position of 1-alkyl-2-acetyl-sn-glycerol.

Despite the marked difference in structure between the neutral acetylated ether-linked glycerolipids of this invention and their enzymatic conversion product, the neutral lipid reduces arterial blood pressure in a similar manner except that larger doses of the neutral lipid are required to obtain a lowering of blood pressure and a longer duration of response is obtained with the neutral lipid. Thus, the neutral lipids of this invention may be utilized alone to obtain blood pressure lowering with sustained duration or in combination, by administering simultaneously or in sequence with the 1-alkyl-2-acetyl-sn-glycero-3-phosphocholine compound preferably in a pharmaceutically acceptable and physiologically inert solvent to heighten the extent of reduction of blood pressure and/or extend the duration of response.

DETAILED DESCRIPTION OF THE INVENTION

Having disclosed the invention in general terms, the following description is provided to show how to chemically synthesize the antihypertensive neutral glycerolipids and how to use them to obtain a desired reduction in arterial pressure. FIG. 1 shows in the lower panel, for reference purposes, the blood pressure change resulting from the administration of 1-hexadecyl-2-acetyl-sn-glycero-3phosphocholine (PAF) as compared to the upper panel which shows the blood pressure response from administering 1-hexadecyl-2-acetyl-sn-glycerol to the same type of animal species.

A—Preparation of the Di-acetyl Derivative of Hexadecylglycerol

1-Hexadecyl-sn-glycerol (>98% purity, obtained from Sigma Chemical Co., St. Louis, MO) was acetylated by heating 200 mg in a solution of 2 ml of acetic anhydride and 0.5 ml of pyridine for 1 hour in a sealed tube at 100° C. After addition of 2 ml of water, the 1-hexadecyl-2,3-diacetyl-sn-glycerol was extracted from the reaction mixture with hexane:diethyl ether (1:1, v/v); the extract was dried over $Na_2SO_4$ and the solvents evaporated with a stream of $N_2$. Only a single component possessing the same $R_f$ as commercial preparations of diacetates of batyl (18:0 alkyl chain) and selachyl (18:1 alkyl chain) alcohols obtained from (Western Chemical Industries, Vancouver, Canada) was found after thin-layer chromatography (TLC) on 250-$\mu$m layers of Silica Gel G developed in chloroform-:methanol (98:1.5, v/v).

1-Hexadecyl-2,3-dipropionyl-sn-glycerol was prepared in the same manner as the 1-hexadecyl-2,3-diacetyl-sn-glycerol except that propionic anhydride was used instead of acetic anhydride.

B—Conversion of the Diacetate Derivatives to 1-alkyl-2-acetyl-sn-glycerol

1-Hexadecyl-2,3-diacetyl-sn-glycerol, the diacetates of selachyl (18:1) and batyl (18:0) alcohols (100 mg of each), and 1-hexadacyl-2,3-dipropionyl-sn-glycerol were treated with 20–25 mg porcine pancreatic lipase obtained from (Nutritional Biochemicals Co., Cleveland, OH) in 2.75 ml of 0.73M Tris-HCl buffer (pH=8.0) that contained 45 mg $CaCl_2$ and 2.5 mg of sodium deoxycholate. The reaction is represented by the following equation:

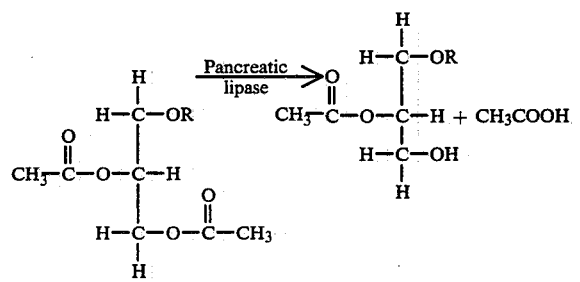

where R represents the long chain alkyl moiety at the sn-1 position.

1-alkyl-2-acetyl-sn-glycerol was a major product of the pancreatic lipase reaction. It was separated and purified from other reaction products by thin layer chromatography, TLC.

After the mixture was shaken vigorously for 2 hours at room temperature, the hydrolytic reaction products were separated on TLC layers prepared with a 4% boric acid solution and developed in chloroform:methanol (98:1.5, v/v). Developed TLC plates were sprayed with a solution of 0.025% rhodamine 6G in ethanol and the resolved lipid components visualized under ultraviolet light. Both isomeric forms of the hydrolytic products produced from the 1-hexadecyl-2,3-acetyl-sn-glycerol (1-hexadecyl-2-acetyl-sn-glycerol and 1-hexadecyl-3-acetyl-sn-glycerol) were isolated from the silica gel by extraction with diethyl ether. NMR provided structural proof of the two isomeric forms of the hexadecyl glycerol. Howver, with the other preparations only the 1-alkyl-2-acetyl-sn-glycerols (derived from selachyl and batyl diacetates) or the 1-alkyl-2-propionyl-sn-glycerol fraction were isolated from the silica gel. After addition of one volume of hexane to the diethyl ether extracts, the organic layers were washed three times with water, dried over $Na_2SO_4$, and the solvent evaporated. The lipid preparations were stored in chloroform at $-20°$ C. The purity of all these compounds was estimated at >98% by TLC analysis.

C—Preparation of Lipid Analogs for Comparison Purposes

A number of other lipid analogs were prepared as described below for testing, including PAF which was used as a reference for comparison purposes. The PAF preparation, 1-hexadecyl-2-acetyl-sn-glycero-3-phosphocholine, was synthesized as previously described in our co-pending application.

An ester analog of PAF, 1-hexadecanoyl-2-acetyl-sn-glycero-3-phosphocholine, was made by acetylation of 1-hexadecanoyl-2-lyso-sn-glycero-3-phosphocholine in a reaction with 0.5 ml of acetic anhydride and 20 mg of 4-dimethylaminopyridine in 1.25 ml of toluene; the sealed tube was heated at 100° C. for 2 hours and, after evaporation of the solvents with a stream of $N_2$, the products were extracted by the method of Bligh and Dyer as described in Canadian Journal of Biochemical Physiology, Vol. 3, pp. 911-917, 1959. The product, 1-hexadecanoyl-2-acetyl-sn-glycerol-3-phosphocholine, was then treated with phospholipase C to produce 1-hexadecanoyl-2-acetyl-sn-glycerol, which was estimated on the basis of TLC to have a purity >95%.

A neutral ether analog of a diradylglycerol with a long chain fatty acid at the sn-2 position, 1-hexadecyl-2-octadecanoyl-sn-glycerol, was isolated by preparative TLC from the reaction products formed after treatment of racemic-hexadecyl-2-octadecenoyl-glycerophosphocholine obtained from (Bioechemisches Labor, Bern, Switzerland) with phospholipase C.

Also, for comparison purposes, an isomer of the 1-hexadecyl-2-acetyl-sn-glycerol was prepared with the acetate at the sn-3 position instead of the sn-2 position.

D—Tests of Blood Pressure

Male (10-month-old) spontaneous hypertensive (SHR) or (1-year-old) normotensive (WKY) rats (both from Charles River Breeding Laboratories, Inc., Wilmington, MA) were used for measurements of mean arterial pressure (MAP) before and after administration of the test substances. The animals were anesthetized with sodium pentobarbital and connected to a pressure transducer inserted into the descending aorta of the test animal and the blood pressure tracings were obtained with a physiograph. All neutral lipid preparations tested for their effect on blood pressure were dissolved at a concentration of 100 nanomoles(nmol)/0.1 ml of 1% Tween-20 (polyoxyethylene sorbitan monolaurate, a commercially available emulsifier) in saline and then injected into the vena cava over a period of a few seconds and the blood pressure continuously monitored.

E—Results

A typical blood pressure response curve after an intravenous injection of 100 nanomoles (i.e., $10^{-9}$ moles) of the 1-hexadecyl-2-acetyl-sn-glycerol is shown in the upper panel of FIG. 1. As shown, the mean arterial pressure (MAP) began to decrease approximately 5 seconds after injection of 1-hexadecyl-2-acetyl-sn-glycerol and reached a maximum depression 1 to 2 minutes later; the arterial pressure returned to pre-injection levels within about 15 minutes. Repeated injections of the 1% Tween-20 solution alone (i.e., without lipid) did not affect the MAP.

We were unable to detect any changes in heart rate during the antihypertensive response elicited by 1-hexadecyl-2-acetyl-sn-glycerol ($309\pm31$ beats/minute before injection and $294\pm21$ beats/minute after four separate injections of the active compound). For comparison, a tracing of the MAP response obtained after an intravenous injection of 100 picomols of the PAF, 1-hexadecyl-2-acetyl-sn-glycero-3-phosphocholine (in a 0.25% bovine serum albumin solution), is shown in the lower panel of FIG. 1. It can be seen that PAF lowers the MAP more rapidly and to a greater extent than does 1-hexadecyl-2-acetyl-sn-glycerol, but the duration of the response is considerably longer for the active neutral antihypertensive lipid than with PAF.

The effect of increasing the amounts of the 1-hexadecyl-2-acetyl-sn-glycerol injected is shown in Table I.

TABLE I

| EFFECT OF 1-HEXADECYL-2-ACETYL-sn-GLYCEROL ON THE MEAN ARTERIAL PRESSURE IN THE SHR RATS | | | |
|---|---|---|---|
| 1-Hexadecyl-2-acetyl-sn-glycerol injected (nmol) | Number of Trials (n) | Decrease In MAP (%) | Time To Recover MAP (min) |
| 50 | 3 | 12.3 ± 1.3 | 10.5 ± 0.5 |
| 100 | 6 | 25.5 ± 2.8 | 13.2 ± 1.6 |
| 200 | 8 | 39.5 ± 3.2 | 15.4 ± 2.0 |

Percentages represent the mean value±standard error of the mean.

1-Octadec-9-enyl-2-acetyl-sn-glycerol prepared from the diacetate of selachyl alcohol had about the same effect in lowering the MAP ($40.2\pm0.9\%$ by 200 nmol, n=3) as the same dose of 1-hexadecyl-2-acetyl-sn-glycerol, whereas the 1-octadecyl-2-acetyl-sn-glycerol prepared from batyl alcohol was much less effective ($20.4\pm2.3\%$ by 200 nmol, n=4). Injections of 200 nmol of 1-hexadecyl-sn-glycerol, diacetates of batyl or selachyl alcohol, 1-hexadecanoyl-2-acetyl-sn-glycerol, 1-hexadecyl-2-octadecanoyl-sn-glycerol, or 1-hexadecyl-3-acetyl-sn-glycerol failed to exhibit any significant effect on the MAP of hypertensive SHR (<1% of the overall MAP response when compared with an equivalent amount of 1-hexadecyl-2-acetyl-sn-glycerol).

1-Alkyl-2-acetyl-sn-glycerols also exhibit a hypotensive effect in normotensive rats; the blood pressure tracings obtained after an intravenous administration of 200 nmol of the 1-hexadecyl-2-acetyl-sn-glycerol to one-year-old WKY rats gave essentially the same response pattern as seen in FIG. 1 for the SHR animals, except the recovery of the MAP in the normotensive rats appeared to be somewhat longer than the SHR animals. Intravenous injections of 1-hexadecyl-2-propionyl-sn-glycerol (200 nmol) were also found to elicit an identical hypotensive response (41.3% lower MAP, based on maximum decrease).

Since 1-hexadecanoyl-2-acetyl-sn-glycerol, 1-hexadecyl-sn-glycerol, 1-hexadecyl-3-acetyl-sn-glycerol, 1-alkyl-2,3-diacetyl-sn-glycerols and 1-hexadecyl-2-octadecanoyl-sn-glycerol exhibited no hypotensive activities, our findings support the conclusion that a relatively long chain (C12-18) alkyl ether group at the sn-1 position, an acetate group (or other short chain acyl group such as propionate) at the sn-2 position, and a free hydroxyl group at the sn-3 position of glycerol are the essential requirements for expression of the blood pressure lowering action of this neutral glycerolipid.

Having described the invention in general terms how to make and use the selected class of glycerolipids, our invention is defined in the following claims:

We claim:
1. A method for treating a warm-blooded animal comprising administering to said animal a neutral glycerolipid with a 12 to 20 carbon alkyl group at the sn-1 position, a short carbon chain acyl group at the sn-2 position and a hydroxyl group at the sn-3 position in an amount sufficient to lower the arterial blood pressure of said animal.

2. The method as claimed in claim 1 in which the glycerolipid is selected from the group consisting of 1-alkyl-2-acetyl-sn-glycerol or 1-alkyl-2-propionyl-sn-glycerol.

3. A method for treating a warm-blooded animal comprising administering a composition consisting essentially of a 1-alkyl-2-acetyl (or propionyl)-sn glycerol in combination with a 1-alkyl-2-acetyl-sn-glycero-3-phosphocholine, wherein the 1-alkyl groups contain 12 to 20 carbon atoms, dissolved in an inert pharmaceutically acceptable solvent in amounts sufficient to lower the arterial blood pressure of said animal.

* * * * *